(12) United States Patent
Green et al.

(10) Patent No.: US 10,259,763 B2
(45) Date of Patent: Apr. 16, 2019

(54) TRITYLATED ETHERS

(71) Applicant: Dow Global Technologies LLC, Midland, MI (US)

(72) Inventors: George D. Green, Cary, IL (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/643,100

(22) Filed: Mar. 10, 2015

(65) Prior Publication Data

US 2015/0175513 A1 Jun. 25, 2015

Related U.S. Application Data

(62) Division of application No. 14/127,649, filed as application No. PCT/US2012/043718 on Jun. 22, 2012, now Pat. No. 9,012,706.

(60) Provisional application No. 61/500,648, filed on Jun. 24, 2011.

(51) Int. Cl.
| | |
|---|---|
| C07C 43/205 | (2006.01) |
| C10L 1/185 | (2006.01) |
| C07C 43/20 | (2006.01) |
| C10L 1/00 | (2006.01) |
| C10M 129/16 | (2006.01) |

(52) U.S. Cl.
CPC .......... *C07C 43/2055* (2013.01); *C07C 43/20* (2013.01); *C10L 1/003* (2013.01); *C10L 1/1852* (2013.01); *C10M 129/16* (2013.01); *C10L 2230/16* (2013.01); *C10L 2270/026* (2013.01); *C10M 2207/04* (2013.01); *C10N 2230/10* (2013.01); *C10N 2240/08* (2013.01); *C10N 2270/00* (2013.01)

(58) Field of Classification Search
None
See application file for complete search history.

(56) References Cited

U.S. PATENT DOCUMENTS

| | | |
|---|---|---|
| 5,981,283 A | 11/1999 | Anderson, II et al. |
| 7,858,373 B2 | 12/2010 | Banavali et al. |

FOREIGN PATENT DOCUMENTS

| | | |
|---|---|---|
| EP | 512404 A1 | 11/1992 |
| WO | 2012154646 A1 | 11/2012 |
| WO | 2012154668 A1 | 11/2012 |

OTHER PUBLICATIONS

Ei-ichi Funakubo, Toji Matsui, "Studies on the Utilization of Camphor Oil. V" Nippon Kagaku Kaishi (1921-47) (1938), Vol. 59, No. 3, pp. 451-456.*
Douglas Vernon Nelmar Hardy, "The Introduction of the Triphenylmethyl Group into Phenols. Part II.", J. Chem. Soc., Jan. 1929, pp. 1000-1011.*
Clapp ("The Phosphorescence of Tetraphenylmethane and Certain Related Substances", Journal of the American Chemical Society (1939), 61, pp. 523-524).*
("Phosphor", Hawley's Condensed Chemical Dictionary, published online Mar. 15, 2007).*
Schoepfle, et al., "The Reaction between Triarylmethyl Halides and Phenylmagnesium Bromide. II", vol. 58, pp. 791-794 (1936).
Llewellyn, et al., "The Condensation of Some Tertiary Aryl Substituted Carbinols with Phenol in the Presence of Aluminum Chloride", vol. 60, pp. 59-62, (1938).
Barroeta, et al., "Kinetics and Substituent Effects in Electrophilic Aromatic Substitution. II. Tritylation of Catechol and its Monoether", vol. 31, pp. 2330-2333, (1966).
Chuchani, et al., "Kinetics and Substituent Effects in Electrophilic", J. Organic Chemistry, vol. 31, No. 5, pp. 1573-1576 (1966).
Brickman et al., "The Aldehydic Constituents from the Ethanolysis of Spruce and Maple Woods", J. American Chemical Society, vol. 61, No. 2, pp. 523-524 (1939).
"Index of subjects", J. Chemical Society (Resumed), p. 3012 (1929).
Iddles, et al, "Rearrangement of the Triphenylmethyl Ether of Ortho Cresol: Direct Synthesis of 3-Methyl-4-methoxyphenyltriphenylmethane", J. Am. Chem. Soc., 62 (10), pp. 2757-2759 (1940).

* cited by examiner

*Primary Examiner* — Rosalynd A Keys

(57) ABSTRACT

A compound having formula $(Ph_3C)_mAr(OR)_n$, wherein Ph represents a phenyl group, Ar is an aromatic ring system having from six to twenty carbon atoms, R is $C_1$-$C_{18}$ alkyl or $C_7$-$C_{12}$ aralkyl, m is one or two, and n is an integer from one to four.

2 Claims, No Drawings

TRITYLATED ETHERS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula $(Ph_3C)_mAr(OR)_n$, wherein Ph represents a phenyl group, Ar is an aromatic ring system having from six to twenty carbon atoms, R is $C_1$-$C_{18}$ alkyl or $C_7$-$C_{12}$ aralkyl, m is one or two, and n is an integer from one to four.

The present invention further provides a method for marking a petroleum hydrocarbon or a liquid biologically derived fuel; said method comprising adding to said petroleum hydrocarbon or liquid biologically derived fuel at least one compound having formula $(Ph_3C)_mAr(OR)_n$, wherein Ph represents a phenyl group, Ar is an aromatic ring system having from six to twenty carbon atoms, R is $C_1$-$C_{18}$ alkyl or $C_7$-$C_{12}$ aralkyl, m is one or two, and n is an integer from one to four.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear or branched arrangement. Substitution on alkyl groups of one or more hydroxy or alkoxy groups is permitted. Preferably, alkyl groups are saturated and unsubstituted. An "aryl" group is a substituent derived from an aromatic hydrocarbon compound. An aryl group has a total of from six to twenty ring atoms, unless otherwise specified, and has one or more rings which are separate or fused. Substitution on aryl groups of one or more alkyl or alkoxy groups is permitted. An "aralkyl" group is an "alkyl" group substituted by an "aryl" group. Preferably, the compounds of this invention contain elements in their naturally occurring isotopic proportions.

Ar is an aromatic ring system having from six to twenty carbon atoms and whose substituents include $Ph_3C$ and OR groups, preferably one in which the only substituents are $Ph_3C$ and OR groups. Preferably, Ar is a $C_6$-$C_{12}$ hydrocarbyl aromatic ring system. Preferably, Ar is benzene, naphthalene, biphenyl, phenyl ether, diphenylmethane or one of the preceding systems substituted with alkyl and/or alkoxy groups; preferably benzene. Preferably, n is from one to three, preferably two or three, preferably two. Preferably, R is $C_1$-$C_{18}$ alkyl or $C_7$-$C_{10}$ aralkyl, preferably $C_2$-$C_{16}$ alkyl or $C_7$-$C_9$ aralkyl, preferably $C_3$-$C_{12}$ alkyl or $C_7$-$C_9$ aralkyl, preferably $C_2$-$C_{16}$ alkyl, preferably $C_2$-$C_{12}$ alkyl, preferably $C_3$-$C_{12}$ alkyl, preferably $C_3$-$C_{10}$ alkyl.

Preferably, the compound of this invention is represented by formula (I)

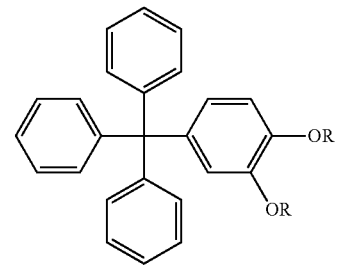

(I)

wherein R is $C_1$-$C_{18}$ alkyl, preferably $C_2$-$C_{18}$ alkyl, preferably $C_2$-$C_{16}$ alkyl, preferably $C_2$-$C_{12}$ alkyl, preferably $C_3$-$C_{12}$ alkyl, preferably $C_3$-$C_{10}$ alkyl.

Preferably, the compound of this invention is represented by formula (II)

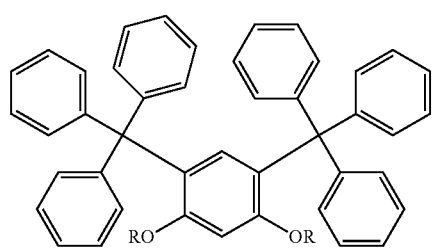

(II)

wherein R is $C_1$-$C_{18}$ alkyl, preferably $C_2$-$C_{18}$ alkyl, preferably $C_2$-$C_{16}$ alkyl, preferably $C_2$-$C_{12}$ alkyl, preferably $C_3$-$C_{12}$ alkyl, preferably $C_3$-$C_{10}$ alkyl.

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., alkylation of phenols or polyhydroxyaromatics with trityl halide or alcohol, followed by alkylation with organic halides in the presence of base. For example, tritylated phenolic ethers may be prepared according to the following reaction scheme,

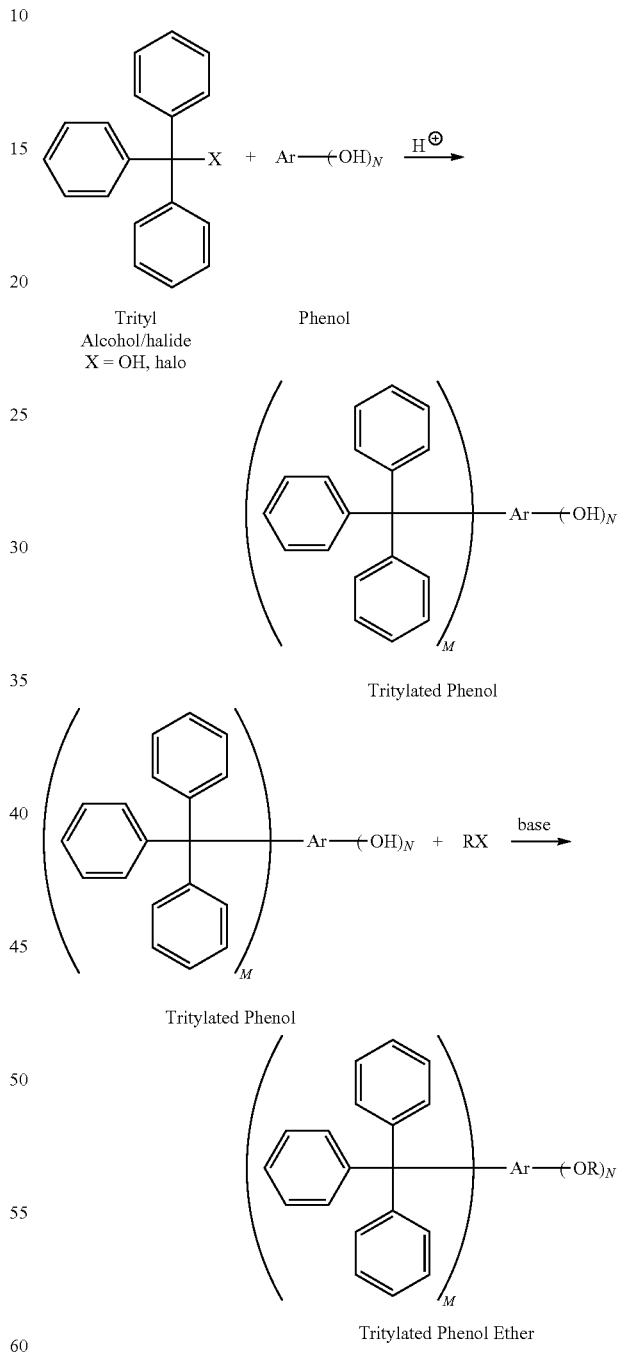

wherein M is one or two and N is 1 to 4.

EXAMPLES

Typical mono-tritylated phenol synthesis procedure is illustrated by the following example:

4-Tritylbenzene-1,2-diol [6331-97-1] (TritCatp)

A 1 L 3-neck flask was equipped with a mechanical stirrer, a reflux condenser with nitrogen blanket, and a heating mantle with a temperature controller and a thermocouple. The flask was charged with 78.20 grams (0.30 moles) of trityl alcohol, 39.39 grams (0.36 moles) of catechol, and 250 mL of glacial acetic acid. The mixture was stirred under nitrogen while heating to about 80° C. A clear amber solution was obtained. To this solution were added 16.73 grams (0.06 moles) of trityl chloride in one portion. The chloride dissolved quickly. The mixture was brought to reflux. After about 30 minutes at reflux, solids began to separate out. Reflux was continued for another 5 hours before cooling to room temperature. The reaction mixture was filtered, and the grey solids were washed on the filter with several portions of acetic acid. The product was dried—first in air and finally in a vacuum oven at 60° C. for 2 hours. The yield of product was 92.0 grams (72.5%), having a melting point of 245-248° C. The structure was confirmed by IR, $^1$H- and $^{13}$C-NMR, and GC/MS analyses.

Typical bis-tritylated phenol synthesis procedure is illustrated by the following example:

4,6-Ditritylbenzene-1,3-diol (Bis-Trit-Res)

A 1 L 3-neck flask was equipped with a mechanical stirrer, a reflux condenser with nitrogen blanket, and a heating mantle with a temperature controller and a thermocouple. The flask was charged with 12.39 grams (0.0475 moles) of trityl alcohol, 15.03 grams (0.054 moles) of trityl chloride, 5.53 grams (0.05 moles) of resorcinol, and with 50 mL of glacial acetic acid. The mixture was stirred under nitrogen while heating to reflux. At about 80° C., a clear amber solution was obtained. Solids began to separate out after about 30 minutes. Reflux was continued for a total of about 34 hours. The reaction mixture was cooled to room temperature, then it was filtered. The white solids were washed on the filter with several portions of acetic acid. The product was dried—first in air for about 2 hours, and then in a vacuum oven at 50° C. for 3 hours. The yield of product was 15.27 grams (95%), having a melting point of 272-274° C. The structure was confirmed by IR, $^1$H- and $^{13}$C-NMR, and GC/MS analyses.

Typical mono-tritylated phenol ether synthesis procedure is illustrated by the following example:

((3,4-Bis(hexyloxy)phenyl)methanetrityl)tribenzene (BHex-TCatp)

A 100 mL 3-neck flask was equipped with a magnetic stirrer, a reflux condenser with nitrogen blanket, and a heating mantle with a temperature controller and a thermocouple. The flask was charged with 3.52 grams (0.01 moles) of 4-tritylbenzene-1,2-diol, 1.32 grams (0.02 moles, 85 wt. %) of potassium hydroxide pellets, and with 25 mL of dimethylsulfoxide. The mixture was stirred under nitrogen while heating to 105° C. After about 20 minutes, all of the potassium hydroxide had dissolved, and the mixture was cooled to 70° C. 1-Bromohexane (3.30 grams, 0.02 moles) was then added in one portion. An exotherm to about 88° C. was observed. After the exotherm subsided, the reaction mixture was maintained at 75° C. for about 1.5 hours. A sample withdrawn for GPC analysis at this point showed no remaining tritylated phenol, indicating that the reaction was completed. The reaction mixture was cooled to <50° C. and was poured into 500 mL of water. Solids precipitated. After stirring at room temperature for about 1.5 hours, the mixture was filtered, and the beige solids were washed on the filter with several portions of water, then they were air-dried. The yield of product was 3.35 grams (64%), having a melting point of 75-77° C. The structure was confirmed by IR, $^1$H- and $^{13}$C-NMR, and GC/MS analyses.

The filtrate from above was milky, and contained additional product which could have been isolated by extraction. In those cases in which, upon quenching the reaction mixture in water, the product separated as an oil, extraction with ethyl ether was used in place of filtration.

Typical bis-tritylated phenol ether synthesis procedure is illustrated by the following example:

((4,6-Bis(hexyloxy)-1,3-phenylene)bis(methanetrityl))hexabenzene (BHex-BTRes)

A 100 mL 3-neck flask was equipped with a magnetic stirrer, a reflux condenser with nitrogen blanket, and a heating mantle with a temperature controller and a thermocouple. The flask was charged with 5.95 grams (0.01 moles) of 4,6-ditritylbenzene-1,3-diol (Bis-Trit-Res), 1.32 grams (0.02 moles, 85 wt. %) of potassium hydroxide pellets, and with 25 mL of dimethylsulfoxide. The mixture was stirred under nitrogen while heating to 105° C. After about 20 minutes, all of the potassium hydroxide had dissolved, and the mixture was cooled to 70° C. 1-Bromohexane (3.30 grams, 0.02 moles) was then added in one portion. An exotherm to about 88° C. was observed. After the exotherm subsided, the reaction mixture was maintained at 75° C. for about 1.5 hours. A sample withdrawn for GPC analysis at this point showed no remaining tritylated phenol, indicating that the reaction was completed. The reaction mixture was cooled to <50° C. and was poured into 500 mL of water. Solids precipitated. After stirring at room temperature for about 1.5 hours, the mixture was filtered, and the beige solids were washed on the filter with several portions of water, then they were air-dried. The yield of product was 4.37 grams (84%), having a melting point of 164-166° C. The structure was confirmed by IR, $^1$H- and $^{13}$C-NMR, and GC/MS analyses.

Using the above procedure, the following tritylated catechol ethers were prepared:

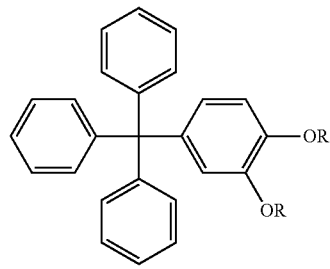

Mono-tritylated catechol ethers

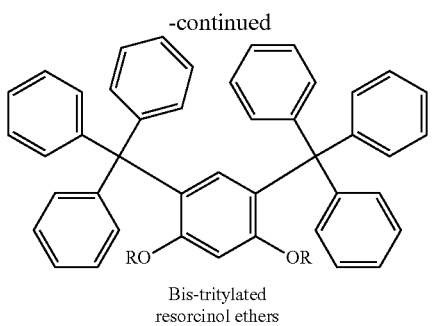

Bis-tritylated
resorcinol ethers

TABLE 1

Synthesis Data for Tritylated Catechol Ethers

| | % Yield | MP, °C. |
|---|---|---|
| Mono-Tritylated Catechol Ethers: R= | | |
| n-$C_4H_9$ | 77.4 | 79-80.5 |
| n-$C_5H_{11}$ | 92.5 | (oil) |
| n-$C_6H_{13}$ | 64 | 75-77 |
| n-$C_7H_{15}$ | 88 | 67-69 |
| n-$C_8H_{17}$ | 79.7 | 58-62 |
| Bis-Tritylated Resorcinol Ethers: R= | | |
| n-$C_6H_{13}$ | 94 | 272-274 |

TABLE 2

Stability and Extractability* data for
Fuel Marker Candidate BHex-TCatp

| Sample | Marker Area % | Internal Standard area % C30 | ratio | Marker % | Change % |
|---|---|---|---|---|---|
| std sample | 292845 | 347044 | 0.84 | 100.00 | 0.00 |
| 5% NaOH | 284966 | 347629 | 0.82 | 97.15 | −2.85 |
| 50% NaOH | 300708 | 354885 | 0.85 | 100.42 | 0.42 |
| 5% $H_2SO_4$ | 300688 | 353739 | 0.85 | 100.73 | 0.73 |
| 98% $H_2SO_4$ | 166305 | 362121 | 0.46 | 54.43 | −45.57 |
| 2% Charcoal | 294103 | 347771 | 0.85 | 100.22 | 0.22 |
| 5% bleach | 295119 | 349006 | 0.85 | 100.21 | 0.21 |
| 2% Metal specs | 288374 | 346719 | 0.83 | 98.57 | −1.43 |

*Test Protocols: 2000 mg/kg solution with internal standard was made in xylenes, then dosed with 5% by weight of 5% NaOH, 50% NaOH, 5% sulfuric acid and 98% sulfuric acid. It was also tested with 2% charcoal 5% bleach and 2% metal specs by wt/wt.

GC Sensitivity and Repeatability Data for BHex-TCatp
Method Evaluation for BHex-TCatp in Diesel 2:

| Stock | Stock(mg/ml) | SubStock(ug/ml) |
|---|---|---|
| BHex-TCatp | 0.26 | 5.11 |

6.39 mg in 25 ml DCM, 0.5 ml Stock in 25 ml Diesel

| Standard | 1 | 2 | 3 | 4 | 5 |
|---|---|---|---|---|---|
| Substock (ul) | 200 | 400 | 600 | 800 | 1000 |
| BHex-TCatp(ug/L) | 102 | 204 | 307 | 409 | 511 |

Linearity and Accuracy:

| Standard | Conc(ppb) | Area (520 + 443) | Conc.(ppb) | % Recovery |
|---|---|---|---|---|
| 1 | 102 | 52537 | 101.9 | 99.7 |
| 1 | 102 | 50989 | 98.9 | 96.7 |
| 2 | 204 | 102479 | 198.5 | 97.1 |
| 2 | 204 | 107034 | 207.3 | 101.4 |
| 3 | 307 | 159596 | 309.0 | 100.7 |
| 3 | 307 | 161848 | 313.4 | 102.2 |
| 4 | 409 | 213638 | 413.5 | 101.1 |
| 4 | 409 | 212133 | 410.5 | 100.4 |
| 5 | 511 | 263991 | 511.0 | 100.0 |
| 5 | 511 | 259911 | 503.1 | 98.4 |

Repeatability and Accuracy:

| | Concentration 307 ppb | | |
|---|---|---|---|
| Rep | Area | Conc.(ppb) | % Recovery |
| 1 | 155936 | 301.9 | 98.4 |
| 2 | 155981 | 302.0 | 98.5 |
| 3 | 157936 | 305.8 | 99.7 |
| 4 | 157497 | 304.9 | 99.4 |
| 5 | 152073 | 294.5 | 96.0 |
| 6 | 157354 | 304.7 | 99.3 |
| Avg. | 156130 | 302.3 | 98.6 |
| Std Dev | 2152 | 4.16 | 1.36 |
| RSD | 1.38 | 1.38 | 1.38 |

Notes:
1. SIM: 520 + 443
2. Solvent: commercial diesel fuel
3. Method:
AGILENT DB-35 - 15 meter × 0.25 mm × 0.25 μm
sample size = 3 μL
flow rate = 1.5 mL/min
initial temp = 100 C.
rate 1 = 20 C./min
final temp 1 = 280 C.
hold = 10 min
rate 2 = 20 C./min
final temp 2 = 340 C.
hold = 6 min
inlet temp = 280 C.
Oven: 100-20 C./min-280(10)-20 C./min-340(4), 3 μl,
Viscosity delay: 1 sec.
Solvent delay: 18 min
Split open: 16 min Plotting Area (y) against concentration (x) from the linearity data above gave a straight line with equation y=516.9259x+135.9, with $R^2$=0.9991.

The invention claimed is:

1. A compound having formula $(Ph_3C)_m Ar(OR)_n$, wherein Ph represents a phenyl group, Ar is a $C_6$-$C_{12}$ hydrocarbyl aromatic ring system, m is two, n is an integer from one to three and R is $C_2$-$C_{18}$ alkyl.

2. The compound of claim 1 in which Ar is a benzene ring system, n is two, and R is $C_3$-$C_{12}$ alkyl.

* * * * *